United States Patent [19]
Edelman et al.

[11] Patent Number: 5,766,584
[45] Date of Patent: Jun. 16, 1998

[54] INHIBITION OF VASCULAR SMOOTH MUSCLE CELL PROLIFERATION WITH IMPLANTED MATRIX CONTAINING VASCULAR ENDOTHELIAL CELLS

[75] Inventors: Elazer R. Edelman, Brookline, Mass.; Aruna Nathan, Plainsboro, N.J.; Matthew A. Nugent, Bedford, Mass.

[73] Assignee: Massachusetts Institute of Technology, Cambridge, Mass.

[21] Appl. No.: 458,978

[22] Filed: Jun. 2, 1995

[51] Int. Cl.$^6$ .......................... C12N 11/00; C12N 11/08; C12N 5/00
[52] U.S. Cl. .......................... 424/93.7; 424/425; 424/426; 435/174; 435/177; 435/180; 435/395; 435/397; 435/398; 435/402
[58] Field of Search .......................... 435/174, 177, 435/180, 182, 240.23, 395, 397, 398, 402; 424/93.7, 422, 423, 425, 426; 514/56

[56] References Cited

U.S. PATENT DOCUMENTS

| | | | |
|---|---|---|---|
| 4,418,691 | 12/1983 | Yannas et al. | 128/156 |
| 4,787,900 | 11/1988 | Yannas | 623/1 |
| 5,399,665 | 3/1995 | Barrera et al. | 528/354 |
| 5,455,039 | 10/1995 | Edelman et al. | 424/422 |
| 5,527,532 | 6/1996 | Edelman et al. | 424/422 |
| 5,540,928 | 7/1996 | Edelman et al. | 424/422 |
| 5,567,612 | 10/1996 | Vacanti et al. | 435/240.23 |

OTHER PUBLICATIONS

Bjornsson et al., "Acidic Fibroblast Growth Factor Promotes Vascular Repair," *Proc. Natl. Acad. Sci. USA*, 88: 8651–8655 (1991).

Castellot et al., "Cultured Endothelial Cells Produce a Heparinlike Inhibitor of Smooth Muscle Cell Growth," *J. Cell Biol.*, 90: 372–9 (1981).

Cooke et al., "Cellular Mechanisms of Atherogenesis and the Effects of Nitric Oxide," *Curr. Opin. Cardiol.*, 7:799–804 (1992).

Edelman, E.R. & Karnovsky, M.J. "Contrasting Effects of the Intermittent and Continuous Administration of heparin in Experimental Restenosis," *Circ.* 89: 770–776 (1994).

Edelman, et al., "Basic Fibroblast Growth Factor Enhances the Coupling of Intimal Hyperplasia and Proliferation of Vasa Vasorum in Injured Rat Arteries," *J. Clin. Invest.* 89:465–471 (1992).

Ellis et al., "Effect of 18–to 24–hour Heparin Administration for Prevention of Restenosis After Uncomplicated Coronary Angioplasty," *Am. Heart. J.*, 117: 777–782 (1989).

Farndale, et al., "Improved Quantitation and Discrimination of Sulphated Glycosaminoglycans by Use of Dimethylmethylene Blue," *Biochimica et Biophysica Acta* 883:173–177 (1986).

Fishman et al., "Endothelial Regeneration in the Rat Carotid Artery and the Significance of Endothelial Denudation in the Pathogenesis of Myointimal Thickening," *Lab. Invest.*, 32: 339–51 (1975).

Gimbrone, M., "Culture of Vascular Enendothelium," *Progress Hemostasis and Thrombosis* 3:1–28 (1976).

McNamara, et al., "L–Arginine Inhibits Balloon Catheter-Induced Intimal Hyperplasia," *Biochem. Biophys. Res. Comm.*, 193: 291–296 (1993).

Moncada et al., "The L–Arginine–Nitric Oxide Pathway," *N. Engl. J. Med.*, 329: 2002–2012 (1993).

Nugent et al., "Vascular Cell–Derived Heparan Sulfate Shows Coupled Inhibition of Basic Fibroblast Growth Factor Binding and Mitogenesis in Vascular Smooht Muscle Cells," *Circulation Research*, 73: 1051–1060 (1993).

Schwartz et al., "The Aortic Intima. II. Repair of the Aortic Lining After Mechanical Denudation," *Am. J. Pathol.*, 81: 15–42 (1975).

*Primary Examiner*—David M. Naff
*Attorney, Agent, or Firm*—Arnall Golden & Gregory, LLP

[57] ABSTRACT

A composition and method are provided for inhibition of vascular smooth muscle cell proliferation following injury to the endothelial cell lining of a blood vessel such as resulting from angioplasty, vascular bypass surgery or organ transplantation. The composition is a matrix such as a biodegradable hydrogel made of a synthetic polymer, protein or polysaccharide seeded with vascular endothelial cells which can be xenografts, allografts or autografts, or genetically engineered cells. Attachment of cells to the matrix can be enhanced by coating with collagen, laminin, fibronectin, fibrin, basement membrane components or attachment peptides. Biologically active compounds such as anti-inflammatory agents may also be contained in the matrix. In the method, the matrix containing endothelial cells is implanted in a patient at a site adjacent the injury such as by wrapping the matrix around the blood vessel. The endothelial cells secrete products that diffuse into surrounding tissue but do not migrate to the endothelial cell lining of the blood vessel. The endothelial cells may be obtained by biopsy of the patient into which the matrix is implanted and the cells can be cultured in the matrix in vitro and then implanted in vivo.

19 Claims, 2 Drawing Sheets

INHIBITION OF VASCULAR SMOOTH MUSCLE CELL PROLIFERATION WITH IMPLANTED MATRIX CONTAINING VASCULAR ENDOTHELIAL CELLS

BACKGROUND OF THE INVENTION

The United States government has rights in this invention by virtue of National Institutes of Health grants GM/HL 49039 and AG00294, to Elazer R. Edelman.

The present invention is generally in the area of methods for inhibiting or preventing vascular smooth muscle cell proliferation, or restenosis, following vascular intervention or injury, such as angioplasty, vascular bypass surgery, organ transplantation, or other vascular intervention or manipulation.

Angioplasty, surgery and other vascular intervention are complicated by an accelerated arteriopathy characterized by rapid growth of cells into the lumen within a short period of time which is severe enough to jeopardize the blood flow to distal organs.

Vascular bypass surgery has been widely used to correct stenotic and occluded blood vessels, as when plaques develop on the surface of blood vessels in atherosclerosis. In bypass surgery, one or more healthy blood vessels are grafted into the occluded vessels at either end of the occlusion to shunt blood around the stenotic or occluded vessel to re-establish a sufficient blood supply to the tissue whose blood supply is endangered by the stenosis or occlusion. This surgery often successfully revascularizes the endangered tissue.

In recent years, angioplasty has been developed as an alternative treatment to bypass surgery, especially in patients who have been diagnosed early in the development of stenosis or occlusion of blood vessels due to the abnormal laying down of plaque on the endothelial wall of a blood vessel. Angioplasty typically involves guiding a catheter which is usually fitted with a balloon or expandable metal mesh up through an artery to the region of stenosis or occlusion and the brief inflation, one or more times, of the balloon or wire mesh to push the obstructing intravascular material or plaque up against the endothelial wall of the vessel, thereby compressing and/or breaking apart the plaque and reestablishing blood flow. However, angioplasty treatment can injure the vessel, especially when the balloon is overinflated or the mesh overextended, causing a variety of undesirable results, such as denudation (removal) of the endothelial cell layer in the region of the angioplasty, dissection of part of the inner vessel wall from the remainder of the vessel with accompanying occlusion of the vessel, or rupture of the tunica intima layer of the vessel.

Though the hallmark of the rapidly accelerating lesions following angioplasty, vascular bypass grafting, and organ transplantation is the proliferation of smooth muscle cells and their accumulation within the tunica intima, it is the loss of normal endothelial function that heralds these events and may stimulate them to occur. The arterial endothelium serves as a transport barrier, a biochemical filter and as a regulator of many vascular phenomena. The most potent vasodilators, thromboresistant compounds and inhibitors of smooth muscle cell proliferation, are endothelial derived. Vascular smooth muscle cell accumulation within the intima ceases with restoration of the endothelium (Schwartz et al.,*Am. J. Pathol.*, 81: 15–42 (1975); Fishman et al., *Lab. Invest.*, 32: 339–51 (1975)) and regression of intimal hyperplasia is maximized where endothelial restoration is maximized (Bjornsson et al., *Proc. Natl. Acad. Sci. USA*, 88: 8651–8655 (1991)). Confluent, and not exponentially growing, endothelial cells produce a series of compounds that are the most potent vasodilators, inhibitors of spasm, and inhibitors of smooth muscle cell proliferation. Heparan sulfate proteoglycan produced by the endothelial cells has multitudinous effects on the smooth muscle cells including interfering with binding of heparin-binding growth factors (Nugent et al., *Circulation Research*, 73: 1051–1060 (1993), which are known to stimulate vascular smooth muscle cell growth (Nugent et al., *Circulation Research*, 73: 1051–1060 (1993); Castellot et al., *J. Cell Biol.*, 90: 372–9 (1981)). It appears, therefore, that restoring the endothelial monolayer of a blood vessel restores the agents or compounds responsible for biochemical control of vascular cell proliferation.

Other efforts at limiting the undesirable proliferative and disease states of vascular endothelium have focused on the isolated administration of analogs of endothelial compounds. Certain drugs, such as heparin, are especially effective inhibitors of vascular smooth muscle cell proliferation in tissue culture and animal models of arterial diseases precisely because they mimic the activity of natural endothelial-derived compounds like heparan sulfate proteoglycan, Edelman, E.R. & Karnovsky, M. J. *Circ.* 89: 770–776 (1994). However, despite cell culture and small animal data supporting the regulatory role of heparin-like compounds, exogenous heparin preparations have shown no benefit in human trials. For example, when patients were randomized to heparin or dextrose infusion over the first 18 to 24 hours post angioplasty, 41.2% of the heparinized patients and only 36.7% of the dextrose infusion patients had evidence for restenosis (Ellis et al., *Am. Heart. J.*, 117: 777–782 (1989)). Moreover, bleeding complications were twice as frequent in the heparinized group. In another trial, angioplasty patients injected subcutaneously with heparin at 10,000 IU/day had 2.5 fold more restenosis and significantly more ischemic complications than patients treated in the standard fashion (Lehmann et al., *J. Am. Coll. Cardiol.*, 17: 181A (abstract) (1991)). Non-heparin endothelial compounds such as nitric oxide and the prostaglandins are potent regulators of a range of biologic effects involving smooth muscle cells. Inhibitors of these compounds have been shown to control intimal hyperplasia following experimental vascular injury (Cooke et al., *Curr. Opin. Cardiol.*, 7: 799–804 (1992); Moncada et al., *N. Engl. J. Med.*, 329: 2002–2012 (1993); McNamara, et al., *Biochem. Biophys. Res. Comm.*, 193: 291–296 (1993)). This is indicative that the vascular endothelium is a powerful regulator of the blood vessel wall, not because of the production and secretion of one compound alone, but because of its presence as an intact unit. While concerns have been raised as to the difference in protocols allowing for benefit in animals and worsening of disease in man (Edelman et al., Circulation, 89: 770–776 (1994)), it appears likely that a single endothelial product, such as heparin, is incapable of replacing the entire endothelium in the control of complex human vascular lesions.

Accordingly, there is a need for means and methods of promoting healing of vascular tissue and controlling vascular muscle cell proliferation (hyperplasia) to prevent restenosis of blood vessels after angioplasty, vascular bypass, organ transplantation, or vascular disease without the risk of rapid reocclusion.

It is therefore an object of the present invention to provide a means of preventing occlusion following vascular intervention.

It is a further object of the present invention to provide methods for understanding and controlling the mechanisms of restenosis and vascular occlusion.

SUMMARY OF THE INVENTION

Compositions and methods for inhibiting excessive intimal growth (hyperplasia) and/or vascular smooth muscle cell proliferation (hyperplasia) following intravascular intervention or injury are disclosed. In the preferred embodiment, endothelial cells are present in or on a biocompatible, biodegradable or non-biodegradable matrix, which allows the cells to reside and secrete products into the surrounding tissue or into the matrix, from which they can diffuse into the surrounding tissue. The endothelial cell-matrix composition is juxtaposed with the target blood vessel, which might be injured, for example, from angioplasty, surgery, transplantation or atherosclerosis, to inhibit subsequent restenosis or occlusion of the blood vessel.

DETAILED DESCRIPTION OF THE INVENTION

The compositions described herein for inhibition of intimal hyperplasia consist of a matrix, most preferably a hydrogel, seeded with endothelial cells which can be xenografts, allografts or autografts, which is implanted at a site near to or at the region of hyperplasia at the time of vascular intervention or upon diagnosis of restenosis or other occlusion of a blood vessel.

COMPOSITIONS TO INHIBIT INTIMAL HYPERPLASIA

The compositions described herein are used to inhibit undesired response to vascular injury that includes hyperplasia of smooth muscle vascular cells which occurs in response to injury to the endothelial tissue of blood vessels, for example, as a result of angioplasty, coronary artery bypass used to open a stenotic or occluded vessel. Vascular smooth muscle cell hyperplasia triggered by the injured endothelium can result in restenosis of the blood vessel due to the excessive proliferation of vascular smooth muscle cells.

Cells

Endothelial cells are isolated by standard methods, for example, as described by Gimbrone, M. Culture of vascular endothelium. *Progress Hemostasis and Thrombosis* 3:1–28 (1976). Cells can be obtained at the time of the procedure using standard biopsy techniques, whether the procedure is angioplasty, open field surgery or for diagnostic purposes. The cells can be dissociated with collagenase or trypsin and seeded directly into a matrix as described below for immediate implantation, or cultured in vitro as required to generate the number of cells to be implanted. The cells are typically seeded into or onto the matrix at a density of between approximately $10^3$ and $10^{12}$ cells/cm$^3$. Cell densities can be determined using visual methods or a Coulter counter.

The effective amount of cells and matrix to be administered is that which prevents or inhibits hyperplasia at the site of vascular injury.

Other cells which are genetically engineered, using oligonucleotides resulting in ribozyme-mediated cleavage of targeted genes or regulatory elements, or antisense to block transcription of targeted genes, or sequences encoding defective, missing or insufficient genes, can also be used. For example, cells transfected with genes for synthesis of heparan sulfate, regulators of heparan sulfate, nitric oxide synthase, growth factors, cytokines and other vasoregulatory products could be seeded into the matrix and implanted. Genes can be transfected into the cells using standard methodology such as viral vectors, microinjection and calcium phosphate precipitation.

Other materials can also be administered via the matrix, including anti-inflammatory agents, prostaglandins, prostanoids, angiotensin and related compounds, tyrosine kinase inhibitors, immunosuppressants, vitamins, glucocorticoids, anti-oxidants, free radical scavengers, peptide hormones, angiogenic and angiogenic inhibitory factors.

The Matrix

The endothelial cells are seeded onto or into a biocompatible matrix which is suitable for implanting in contact adjacent to or at the site of the vascular injury, for example, by wrapping around the blood vessel. The matrix can be in the form of a gel, foam, suspension, microcapsules, solid polymeric support, or fibrous structure. The matrix may also serve in a physically supporting role. There is no specific requirement as to thickness, size or shape. When the cells are seeded within the matrix, it is preferred that the matrix be sufficiently porous to allow free diffusion of nutrients and gases into the matrix to maintain cell viabilility, while allowing the secretory products of the cells to diffuse out of the matrix into the surrounding tissue in roughly physiologically quantities. The matrix may also serve to protect non-autologous cells from immune attack.

Preferably, the matrix is a biodegradable material, such as a synthetic polymer degrading by hydrolysis, for example, polyhydroxy acids like polylactic acid, polyglycolic acid and copolymers thereof, polyorthoesters, polyanhydrides, proteins such as gelatin and collagen, or carbohydrates or polysaccharides such as cellulose and derivatized celluloses, chitosan, alginate, or combinations thereof, so that over the course of several days or weeks after implantation of the matrix material, the matrix gradually disappears. In a preferred embodiment, the matrix is a hydrogel, defined as a matrix wherein typically approximately 900 by weight of the matrix is absorbed water. Hydrogels can be formed by ionic or covalent crosslinking of a variety of water soluble polymers such as polyphosphazenes, polysaccharides such as alginate, and proteins such as gelatin. As demonstrated in the following examples, a presently preferred matrix material is purified gelatin-based Gelfoam™ (The Upjohn Co., Kalamazoo, Mich.) surgical sponge.

The use of biodegradable matrices eliminates the need for surgery to remove undegraded implanted matrix, after regression of the hyperplasia and healing of the endothelial injury. However, synthetic non-biodegradable matrices may also be used. Useful materials include ethylene vinyl acetate, polyvinyl alcohol, silicone, polyurethane, non-biodegradable polyesters, and polyethyleneoxide-polypropyleneoxide, and tetrafluoroethylene meshes (Teflon®).

Attachment of the cells to the matrix can be enhanced by coating or chemically modifying, attaching or derivatizing the polymer with a material such as collagen, laminin, fibronectin, fibrin, basement membrane components, and attachment peptides (RGD and many others are known and described in the literature).

Culturing of Cells in Matrix

The matrix material seeded with endothelial cells can be cultured in vitro to promote cell growth throughout the matrix. At various times during incubation of the seeded matrix in the culture medium, samples of seeded matrix can be removed and examined, for example, by cell staining and microscopic observation, to determine the extent of cell growth and proliferation in the matrix, as well as production of total sulfated glycosaminoglycans and, specifically, heparan sulfate.

When the cells have reached the desired cell density in the matrix or have confluently grown over most of the interstices of the cultured matrix, the matrix is removed from the culture medium and either used in the procedures to treat vascular smooth muscle cell hyperplasia described below, or stored for subsequent implantation.

Alternatively, the matrix is seeded with the cells immediately prior to implantation of the matrix.

METHODS OF TREATING INTIMAL HYPERPLASIA

Patients can be diagnosed for vascular endothelial cell injury using known methods, such as X-ray fluoroscopic examination of dye flowing through a particular region of a blood vessel or other visual techniques, the presence of symptoms such as pain, based on clinical judgment, or signs evidenced physical examination. Alternatively, it can be assumed that injury will arise due to performance of procedures such as angioplasty, arterial bypass graft, peripheral bypass surgery, or organ transplantation and the patient treated based on the assumption that injury or disease will inevitably arise.

In a preferred embodiment, endothelial cell-matrix strips are applied to the site of injury during open field surgery. In this embodiment, the strips of cultured matrix are applied to the exterior of the injured blood vessel over the internal site of injury, usually by wrapping the matrix strips around the vessel. After implantation, the cells remain viable and produce factors such as sulfated glycosaminoglycan, including heparan sulfate.

If intimal hyperplasia had been observed prior to implanting or wrapping the strips of matrices, the regression of hyperplasia is typically evidenced by a decrease in pain or other symptoms of decreased blood flow, or through the use of imaging techniques. The decrease in hyperplasia or increase in flow rate through the injured vessel can be monitored by the same methods used to initially diagnose the injury to the vascular endothelium or blockage of the blood vessel.

The following non-limiting examples illustrate some of the various aspects of compositions and methods used to treat vascular smooth muscle cell hyperplasia and restenosis of blood vessels.

Example 1

Cell Engraftment and Characterization of Cells Cultured in the Seeded Matrix.

Bovine aortic endothelial (BAE) and mutant Chinese hamster ovary (CHO-745) cells were cultured on Gelfoam™ matrices. The mutant cells, obtained from Dr. J. Esko (University of Alabama, Birmingham, AB), served as control cells as they produce no demonstrable heparan sulfate (Esko 1992) and, as a result, unlike endothelial cells, do not inhibit bFGF binding to or mitogenesis of cultured vascular smooth muscle cells (Nugent, et al., 1993). Gelfoam™ has long been used as an implantable surgical sponge and more recently as a scaffolding for cell growth (Centra, et al., 1992). This material, isolated from porcine dermal gelatin, was supplied in blocks (UpJohn Inc.), cut into 2.5×1×0.3 $cm^3$ pieces and hydrated by autoclaving for 10 min in Hanks balanced salt solution (HBSS). Upon cooling, the blocks were placed in 17×100 mm polypropylene tubes to which 2 mL of cell suspension ($0.6 \times 10^5$ cells/mL) was added. The endothelial cells were suspended in Dulbecco's modified Eagle's medium (DMEM) and the CHO-745 cells were suspended in Ham's F-12 medium. Media was supplemented with 1 g/L glucose and 10% calf serum.

Culture tubes were gently agitated to disperse the cells and then incubated at a 45° angle, 37° C., humidified, 5% $CO_2$ and 95% air, for up to 15 days. Growth medium was changed on days 3, 7 and 12. On days 0, 2, 4, 7, 10 and 15, the number of cells in the media (non-adherent cells) and those attached to the Gelfoam™ were determined using a hemocytometer. Prior to counting the attached cells, the Gelfoam™ blocks were washed four times with HBSS to remove non-attached cells and serum. Collagenase (1 mg/mL) was used to digest the Gelfoam™, releasing all the cells from the matrix. An 80 µL aliquot was removed for cell counting and the viability was checked by trypan blue exclusion.

Figure 1:
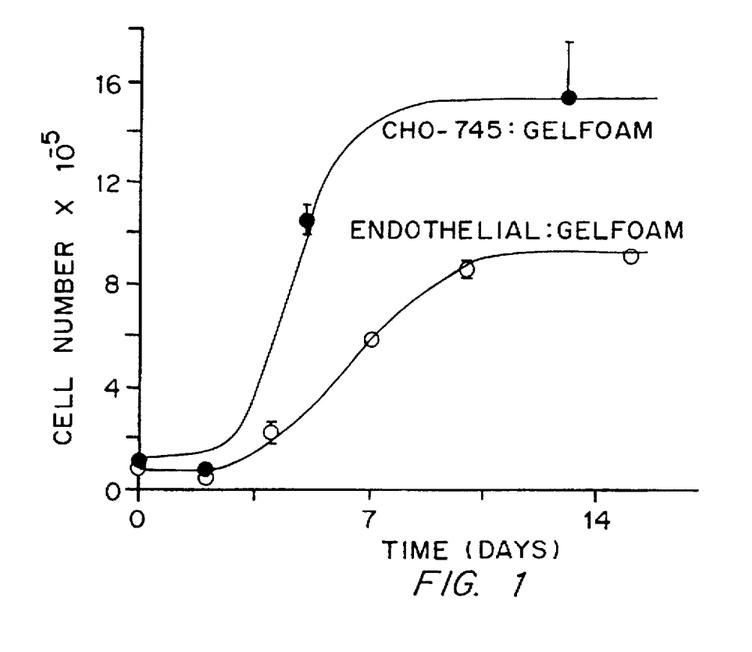
FIG. 1 is a graph of the growth (measured as cell number) of bovine aortic endothelial (BAE) cells (open circles) and Chinese Hamster Ovary 745 cells (controls which do not produce regulators of smooth muscle cell proliferation) (dark circles) on Gelfoam™ (The Upjohn Co., Kalamazoo, Mich.) collagen matrix over time (days).

The results are shown in FIG. 1. Each data point represents the average cell number ± the standard error (SEM) of duplicate determinations.

Cells lined the interstices of this three dimensional collagen-like matrix (Centra, et al., 1992), and remained within the matrices without migrating outward. Cell growth followed a pattern similar to that observed on tissue culture polystyrene. Cell viability as evaluated by trypan blue exclusion remained at 90±2.3% for the BAE cells and 93.1±1.70% for the CHO-745 over the course of the culture.

The preservation of the immune identity of cells within Gelfoam™ blocks recovered 14 days after placement in tissue culture or around rat carotid arteries was determined by immunostaining for the endothelial marker von Willebrand's factor as described by Edelman, et al., J. Clin. Invest. 89:465–471 (1992).

The amount of heparan sulfate in conditioned media produced by cells cultured on Gelfoam™ or tissue culture polystyrene was measured. Gelfoam™ films containing endothelial cells or CHO-745 cells were incubated in culture medium containing no antibiotics and no calf serum for 24 hours at 37° C. As a control, identical Gelfoam™ films without cells were incubated in the respective media. The medium was collected, centrifuged (5,000×g), dialyzed exhaustively against water, and concentrated by lyophilization. Total sulfated glycosaminoglycan was determined using dimethylmethylene blue (Farndale, et al., *Biochimica et Biophysica Acta* 883:173-177 (1986), and the amount of heparan sulfate was assessed after samples were treated with heparinase. The endothelial and CHO-745 cells grown on Gelfoam™ were also radiolabeled with $^{35}SO_4$ (100 μCi/mL, 24 h) to visualize the metabolic synthesis of heparan sulfate by the cells. The medium was collected, centrifuged, and $^{35}SO_4$-proteoglycan separated from the free $^{35}SO_4$ by vacuum filtration through cationic nylon membranes (Rapraeger and Yeaman, *Anal. Biochem.* 179:361-365 (1989)). Filters containing $^{35}SO_4$-proteoglycan were incubated in nitrous acid (0.48M sodium nitrite combined with 3.6M acetic acid) and counted to determine the amount of radioactivity incorporated within heparan sulfate.

Figure 2:
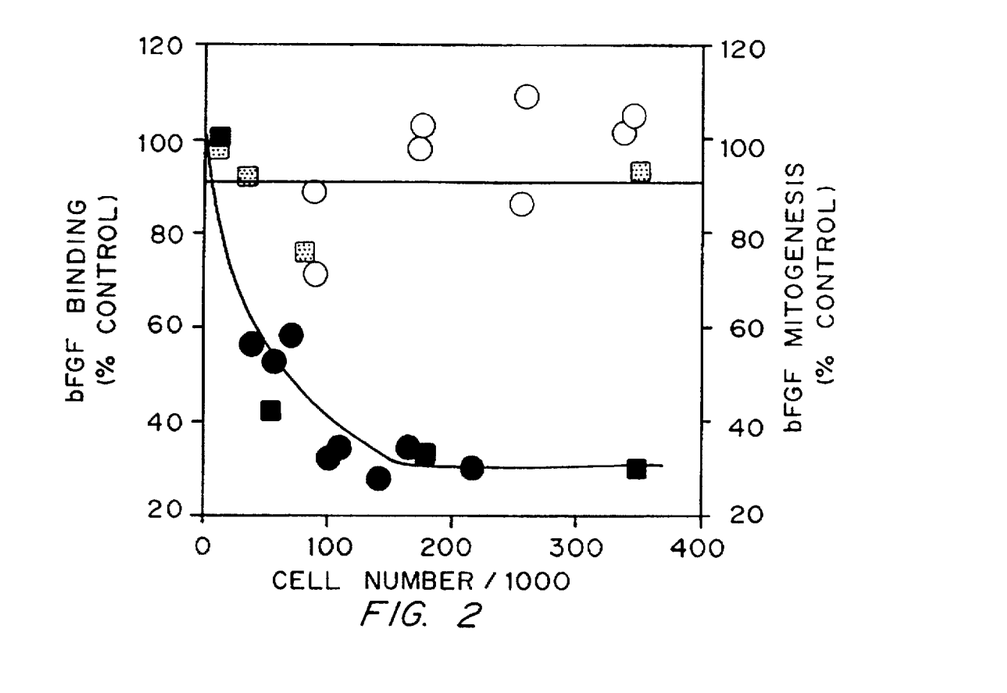
FIG. 2 is a graph of inhibition (% control) of binding (dark circles) and mitogenesis (dark squares) of the potent vascular cell growth promoter bFGF for vascular smooth muscle cells by endothelial cell-Gelfoam® conditioned media, compared with inhibition of bFGF binding (open circles) and mitogenesis (hatched squares) for vascular smooth muscle cells by CHO-745 cell-Gelfoam® conditioned media.

Engrafted cells remained viable with full retention of biochemical secretory ability and biologic potency as well as immunoidentity. Cells cultured on Gelfoam™ produced nearly identical amounts of total sulfated glycosaminoglycan and heparan sulfate as that produced when the same cells were grown on polystyrene dishes. In addition, there was no significant difference in the profile of the proteoglycan when resolved on 5% SDS-PAGE. For both cells grown on Gelfoam™ and tissue culture polystyrene, the majority of the proteoglycan migrated as a band greater than 600 kDa relative to protein standards. When compared to CHO-745 cells grown on Gelfoam™, the engrafted endothelial cells produced an 11.1-fold greater amount of glycosaminoglycan (4.1±0.3 microgram/$10^6$ cells/day for endothelial cells versus 0.37±0.02 microgram/$10^6$ cells/day for CHO-745 cells). While 29.1% of the glycosaminoglycan produced by the endothelial cells was heparan sulfate (1.2±0.05 microgram/$10^6$ cells/day), CHO-745 cells produced no detectable heparan sulfate. Conditioned media from Gelfoam™ engrafted endothelial cells also inhibited both binding of $^{125}I$-bFGF to heparan sulfate proteoglycan and the mitogenic effect of bFGF on vascular smooth muscle cells in a dose dependent fashion, as shown by FIG. 2. In contrast, conditioned media from CHO-745 cells had no effect on binding, and similarly no effect on growth factor induced mitogenesis, as shown by FIG. 2.

Example 2
Inhibition of Intimal Hyperplasia in Rats.
Implantation of Matrix Strips Containing BAE Cells into Rats.

The in vivo effects of engrafted cells in matrix strips were evaluated in an endothelial denuding arterial injury model in Sprague-Dawley rats. Strips of Gelfoam™ gelatin matrix (2.5×1×0.3 cm³ each) containing BAE cells or CHO-745 cells, or no cells, were wrapped around carotid arteries denuded with a balloon catheter, and their effect on smooth muscle cell proliferation and intimal hyperplasia was determined two weeks later.

Endothelial denudation of the left common carotid artery in Sprague-Dawley rats was performed with a 2 French Fogarty balloon catheter introduced through an external carotid arteriotomy and passed three times in its inflated state over the endothelium of the common carotid artery (Edelman, et al., 1992, Clowes, et al., 1983, Edelman, et al., 1990). Strips of Gelfoam™ (2.5×1×0.3 cm³ each) containing BAE cells, CHO-745 cells, or no cells were wrapped around denuded arteries. The strip ends overlapped, ensuring complete encircling of the artery. Fascial planes were sutured closed to further immobilize the devices.

To compare the results of anticipated physiologic secretion of endothelial cell products to the pharmacologic dosing of a proven endothelial-cell analog, hydrogel films were formulated (Nathan, et al., 1994) to release heparin alone at a dose, 2.5±0.1 microgram/day. This dose and mode of delivery has previously been demonstrated to maximize heparin's inhibition of neointimal hyperplasia (Edelman, et al., 1990; Edelman, et al., 1993; Edelman and Karnovsky 1994).

On the 14th post-operative day, animals were euthanized and perfused clear via the left ventricle with Ringer's lactate solution followed by immersion fixation with Carnoy's fixative (60% methanol, 30% chloroform, 10% glacial acetic acid). The location of the implanted matrices was noted and the matrices recovered with the entire length of the intact arteries. The carotid arteries were harvested and cut into five equal segments, three including the Gelfoam™ wrap and segments above and below. Segments were paraffin embedded and 6 micron sections obtained along the length of each segment.

After staining with hematoxylin/eosin or verHoeff's elastin stain, the intimal, medial and adventitial areas, the intima:media area ratio and the percent of luminal occlusion were calculated using computerized digital planimetry with a dedicated video microscope and customized software. Cell proliferation was assayed using immunocytochemical identification of proliferating cell nuclear antigenicity (PCNA) and the thymidine analog 5-bromo-2'-deoxyuridine (BrdU, New England Nuclear, Dupont Corp., Wilmington, Del.) which had been injected intraperitoneally, at 50 mg/kg body weight, 3 and 7 days post-surgery and one hour prior to sacrifice.

Segments of the unwrapped balloon injured artery were compared to Gelfoam™ wrapped segments. Comparisons were made across treatment groups and within treatment groups to allow each animal to serve as its own control. Statistical comparisons were performed using analysis of variance (ANOVA) and subsequent differences among groups using Student's t test. Data was rejected as not significantly different if p values of greater than 0.05 were observed. Data line fits were established using a linear regression and correlation model.

Figure 3:
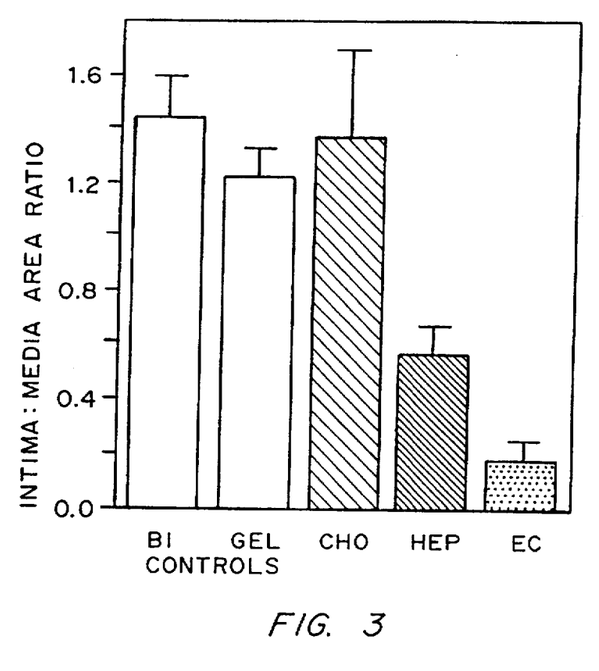
FIG. 3 is a graph of the ratio of the area of the tunica intima to the area of the tunica media after balloon denudation of the endothelium (BI) when the balloon injured arteries were exposed to Gelfoam® alone (Gel), Gelfoam® engrafted with CHO-745 cells (CHO), Gelfoam® containing heparin (Hep), and Gelfoam® containing endothelial cells (EC).

The in vivo potency of the endothelial cell engrafts was retained in addition to their in vitro effects. Balloon denudation of the carotid arterial endothelium led to an increase in the ratio of the area of the tunica intima to the area of the tunica media (I:M) to 1.44±0.16, as shown by FIG. 3. Arterial wall segments exposed to Gelfoam™ containing endothelial cells showed minimal hyperplastic disease. Intimal hyperplasia in arterial segments beneath endothelial cell grafted Gelfoam™ was reduced to 0.17±0.07. This modulating effect was specific to endothelial cells. Control CHO-745 cell engrafts had no statistically significant effect on intimal hyperplasia (I:M 1.36±0.32) compared to balloon injury, alone or empty Gelfoam™ matrices (I:M 1.20±0.11), as shown by FIG. 3.

Heparin has been identified as the gold standard inhibitor of smooth muscle cell proliferation and intimal hyperplasia, in major part because it resembles endothelial-cell-derived heparan sulfate proteoglycan. Indeed the perivascular release of heparin alone from hydrogel films reduced proliferation to an I:M of 0.55±0.11. This result, however, was 3.2 fold less effective than the control exerted by engrafted endothelial cells despite hydrogel release of heparin at twice the rate of release of heparan sulfate proteoglycan from the endothelial implants.

Figure 4:
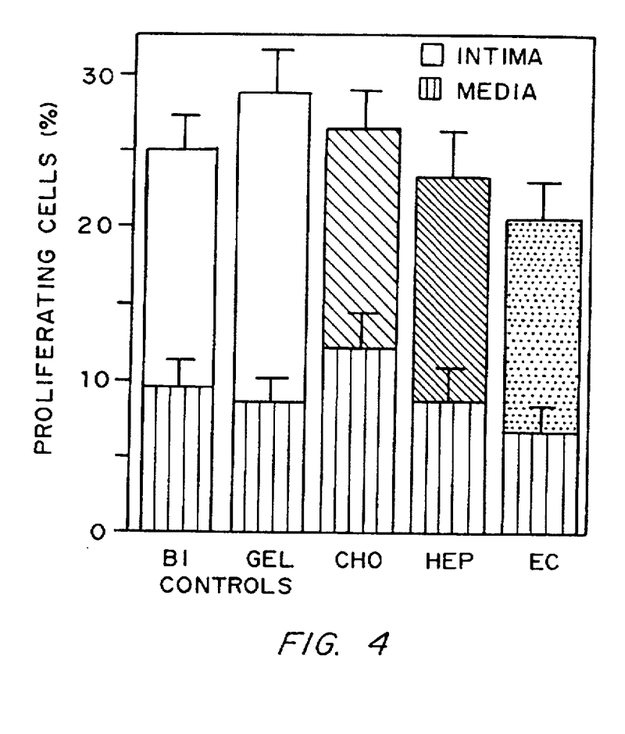
FIG. 4 is a graph showing cell proliferation within both the tunicae intima and media, when exposed to either Gelfoam® engrafted with endothelial cells (EC), Gelfoam® with heparin (Hep), Gelfoam® engrafted with CHO-745 cells (CHO), Gelfoam® control or untreated following balloon angioplasty (BI), comparing the % proliferating cells for the tunica intima (open bar) and tunica media (dark bar).

Gelfoam™ engrafted endothelial cells reduced proliferation as well as intimal hyperplasia. The number of proliferating cells relative to the total number of cells in the tunicae media and intima were used as an index of proliferation. Gelfoam™ implants with engrafted endothelial cells caused a statistically significant decrease in cell proliferation in both the tunica intima (20.4% reduction) and the tunica media (26.3% reduction) relative to empty Gelfoam™ implants, as shown by FIG. 4. Heparin infusion also decreased proliferation but the effect was not statistically significant at the number of animals and sections examined. Relative to balloon injury alone, heparin infusion reduced BrdU immunostaining in the tunica intima by 11.0% and 12.2% in the tunica media, as shown by FIG. 4.

There was no evidence that the implants induced cellular or systemic rejection. The general health and appearance of the animals with the implants was unchanged from controls. Rats subjected to balloon injury alone gained 52.9±3.6 gms over the 14 day experimental period, and those animals that received a cell-free implant hydrated in either DMEM or HAMS-F12 gained 48.0±7.3 gms. The animals implanted with endothelial-seeded implants gained 51.3±2.8 gms and the animals with CHO-745 laden implants gained 53.4±6.5 gms. Rats receiving perivascular heparin gained 56.7±6.2 gms, indicating that the treatment had no side effects.

The results demonstrate the engraftment of endothelial cells on three dimensional biopolymer scaffoldings with preservation of cell viability, normal growth characteristics, immunologic markers, biochemical activity and physiologic effects.

The biologic effects of the engrafted endothelial cells were cell-specific and superior to the infusion of a single pharmacologic analog of an endothelial product, heparin. Conditioned media from implant engrafted endothelial cells, but not heparan sulfate proteoglycan-deficient CHO-745 cells, inhibited bFGF binding to and mitogenesis for vascular smooth muscle cells in a dose dependent fashion. Similarly, only endothelial cell engrafts inhibited intimal hyperplasia. The implant alone or seeded with CHO-745 cells had no statistically significant effect on cell proliferation or intimal hyperplasia. Heparin is one of the most effective anti-proliferative agents for vascular smooth muscle cells, yet even when released at twice the rate of heparan sulfate proteoglycan production by the endothelial cells, intimal hyperplasia and smooth muscle cell proliferation were reduced 3.2 fold less effectively than with the endothelial cell implants.

The control exerted by the endothelial cell implants appears to result solely from the biochemical effects of the engrafted cells. Immunostaining with endothelial cell-specific markers detected no evidence for early recovery of endogenous endothelial cells or the migration of engrafted cells from their biopolymer scaffoldings to the arterial lining in any of the recovered arterial segments. The effects of the implants were localized in a similar manner to the focal effects observed with the perivascular release of other compounds. There was no evidence of a systemic or local immune response or graft rejection.

Modifications and variations of the present invention will be apparent to those skilled in the art from the foregoing detailed description. Such modifications and variations are intended to come within the scope of the appended claims.

We claim:

1. A method of inhibiting mechanisms involved in restenosis of a blood vessel having an endothelial cell lining following injury to the endothelial cell lining of the blood vessel of a patient in need of treatment thereof comprising:

implanting a biocompatible matrix having seeded therein or thereon dissociated vascular endothelial cells at a site adjacent to the injury to the endothelial cell lining, wherein the vascular endothelial cells are provided in an amount effective to inhibit smooth muscle cell proliferation at the site of the injury without migration of the vascular endothelial cells to the endothelial cell lining of the blood vessel.

2. The method of claim 1 wherein the injury arises from angioplasty, coronary artery bypass surgery, peripheral bypass surgery, or organ transplantation.

3. The method of claim 1 wherein the matrix is in a form selected from the group consisting of gels, foams, suspensions, microcapsules, solid polymeric supports, and fibrous structures.

4. The method of claim 1 wherein the cells are obtained by biopsy of the patient into which the matrix is implanted.

5. The method according to claim 1 wherein the matrix is biodegradable.

6. The method of claim 5 wherein the matrix is formed of a material selected from the group consisting of polyhydroxy acids, polyorthoesters, polyanhydrides, proteins, polysaccharides, polyphosphazenes, polyalkylene oxides and combinations thereof.

7. The method of claim 1 wherein the matrix is formed of a material selected from the group consisting of ethylene vinyl acetate, polyvinyl alcohol, silicone, polyurethane, non-biodegradable polyesters, polyethyleneoxide-polypropyleneoxide, tetrafluoroethylene and combinations thereof.

8. The method of claim 1 wherein the matrix further comprises biologically active compounds selected from the group consisting of prostaglandins, prostanoids, tyrosine kinase inhibitors, immunosuppressants, glucocorticoids, anti-oxidants, free radical scavengers, peptide hormones, angiogenic factors, angiogenic inhibitory factors, and combinations thereof.

9. The method of claim 1 wherein the cells are first cultured in the matrix in vitro, then implanted in vivo.

10. The method of claim 1 wherein the matrix is surgically implanted around the blood vessel.

11. A composition for inhibiting mechanisms involved in restenosis of a blood vessel having an endothelial cell lining following injury to the endothelial cell lining of the blood vessel in a patient in need of treatment thereof, comprising a biocompatible matrix shaped for implantation adjacent to a blood vessel, the matrix having seeded therein or thereon dissociated vascular endothelial cells, wherein the vascular endothelial cells are in an amount effective to inhibit smooth muscle cell proliferation at the site of the injury without migration of the vascular endothelial cells to the endothelial cell lining of the blood vessel.

12. The composition of claim 11 wherein the amount is effective to treat an injury arising from angioplasty, coronary artery bypass surgery, peripheral bypass surgery, or organ transplantation.

13. The composition of claim 11 wherein the matrix is in a form selected from the group consisting of gels, foams, suspensions, microcapsules, solid polymeric supports, and fibrous structures.

14. The composition of claim 11 wherein the cells are selected from the group consisting of autologous cells, allograft cells, and xenograft cells.

15. The composition according to claim 4 wherein the matrix is biodegradable.

16. The composition of claim 15 wherein the matrix is formed of a material selected from the group consisting of polyhydroxy acids, polyorthoesters, polyanhydrides, proteins, polysaccharides, polyphosphazenes, and combinations thereof.

17. The composition of claim 11 wherein the matrix is formed of a material selected from the group consisting of ethylene vinyl acetate, polyvinyl alcohol, silicone, polyurethane, non-biodegradable polyesters, polyethyleneoxide-polypropyleneoxide, tetrafluoroethylene, and combinations thereof.

18. The composition of claim 11 wherein the matrix further comprises biologically active compounds selected from the group consisting of prostaglandins, prostanoids, tyrosine kinase inhibitors, immunosuppressants, glucocorticoids, anti-oxidants, free radical scavengers, peptide hormones, angiogenic factors, angiogenic inhibitory factors, and combinations thereof.

19. The composition of claim 14 wherein the cells are genetically engineered.

* * * * *

(12) EX PARTE REEXAMINATION CERTIFICATE (5182nd)
United States Patent
Edelman et al.

(10) Number: US 5,766,584 C1
(45) Certificate Issued: Aug. 16, 2005

(54) INHIBITION OF VASCULAR SMOOTH MUSCLE CELL PROLIFERATION WITH IMPLANTED MATRIX CONTAINING VASCULAR ENDOTHELIAL CELLS

(75) Inventors: Elazer R. Edelman, Brookline, MA (US); Aruna Nathan, Plainsboro, NJ (US); Matthew A. Nugent, Bedford, MA (US)

(73) Assignee: Massachusetts Institute of Technology, Cambridge, MA (US)

Reexamination Request:
No. 90/006,920, Jan. 26, 2004

Reexamination Certificate for:
Patent No.: 5,766,584
Issued: Jun. 16, 1998
Appl. No.: 08/458,978
Filed: Jun. 2, 1995

(51) Int. Cl.$^7$ .......................... A01N 65/00; C12N 11/00; C12N 11/08; C12N 5/00
(52) U.S. Cl. ...................... 424/93.7; 424/425; 424/426; 435/174; 435/177; 435/180; 435/395; 435/397; 435/398; 435/402
(58) Field of Search ............................... 424/93.7, 425, 424/426; 435/174, 177, 180, 395, 397, 398, 402; 514/56

(56) References Cited

U.S. PATENT DOCUMENTS

| | | |
|---|---|---|
| 4,418,691 A | 12/1983 | Yannas et al. |
| 4,732,155 A | 3/1988 | Zetter et al. |
| 4,787,900 A | 11/1988 | Yannas |
| 5,399,665 A | 3/1995 | Barrera et al. |
| 5,455,039 A | 10/1995 | Edelman et al. |
| 5,527,532 A | 6/1996 | Edelman et al. |
| 5,540,928 A | 7/1996 | Edelman et al. |
| 5,567,612 A | 10/1996 | Vacanti et al. |
| 5,716,404 A | 2/1998 | Vacanti et al. |
| 5,736,372 A | 4/1998 | Vacanti et al. |
| 5,739,113 A | 4/1998 | Lee |
| 5,759,830 A | 6/1998 | Vacanti et al. |
| 5,770,193 A | 6/1998 | Vacanti et al. |
| 5,770,417 A | 6/1998 | Vacanti et al. |
| 5,804,178 A | 9/1998 | Vacanti et al. |
| 5,855,610 A | 1/1999 | Vacanti et al. |
| 6,068,837 A | 5/2000 | Shockley et al. |
| 6,139,574 A | 10/2000 | Vacanti et al. |
| 6,140,039 A | 10/2000 | Naughton et al. |
| 6,281,015 B1 | 8/2001 | Mooney et al. |
| 6,309,635 B1 | 10/2001 | Ingber et al. |
| 6,348,069 B1 | 2/2002 | Vacanti et al. |
| 6,358,989 B1 | 3/2002 | Kunz et al. |
| 6,569,441 B2 | 5/2003 | Kunz et al. |
| 6,730,298 B2 | 5/2004 | Griffith-Cima et al. |

FOREIGN PATENT DOCUMENTS

| | | |
|---|---|---|
| EP | 0 341 006 | * 11/1989 |
| EP | 0518389 | 12/1992 |
| WO | WO93/02188 | 2/1993 |
| WO | WO93/14193 | 7/1993 |
| WO | WO95/29713 | 11/1995 |

OTHER PUBLICATIONS

Zarge et al, J Vasc Surg, 25:840–9, 1997.*
Babaei, et al., "Role of Nitric Oxide in the Angiogenic Response in Vitro to Basic Fibroblast Growth Factor," *Circ Res.* 82:1007–1015 (1998).
Bjornsson, et al., "Acidic Fibroblast Growth Factor Promotes Vascular Repair," *Proc. Natl. Acad. Sci. USA* 88:8651–8655 (1991).
Cooke, et al., "Cellular Mechanisms of Atherogenesis and the Effects of Nitric Oxide," *Curr. Opin. Cardiol.* 7:799–804 (1992).
Dodge, et al., "Density–Dependent Endothelial Cell Production of an Inhibitor of Smooth Muscle Cell Growth," *J. Cell. Biochem.* 53:21–31 (1993).
Edelman, et al., "Contrasting Effects of the Intermittent and Continuous Administration of Heparin in Experimental Restenosis," *Circ.* 89(2):770–776 (1994).
Edelman, et al., "Basic Fibroblast Growth Factor Enhances the Coupling of Intimal Hyperplasia and Proliferation of Vasa Vasorum in Injured Rat Arteries," *J. Clin. Invest.* 89:465–473 (1992).
Ellis, et al., "Effect of 18– to 24–hour Heparin Administration for Prevention of Restonosis After Uncomplicated Coronary Angioplasty," *Am. Heart. J.* 117(4):777–782 (1989).
Farndale, et al., "Improved Quantitation and Discrimination of Sulphated Glycosaminoglycans by Use of Dimethylmethylene Blue," *BioChemica et Biophysica Acta* 883:173–177 (1986).
Fishman, et al., "Endothelial Regeneration in the Rat Carotid Artery and the Significance of Endothelial Denudation in the Pathogenesis of Myointimal Thickening," *Lab. Invest.* 32(3):339–351 (1975).
Gimbrone, M., "Culture of Vascular Endothelium," *Prog. Hemo. and Thromb.* 3:1–28 (1976).

(Continued)

Primary Examiner—Dave Trong Nguyen (57) ABSTRACT

A composition and method are provided for inhibition of vascular smooth muscle cell proliferation following injury to the endothelial cell lining of a blood vessel such as resulting from angioplasty, vascular bypass surgery or organ transplantation. The composition is a matrix such as a biodegradable hydrogel made of a synthetic polymer, protein or polysaccharide seeded with vascular endothelial cells which can be xenografts, allografts or autografts, or genetically engineered cells. Attachment of cells to the matrix can be enhanced by coating with collagen, laminin, fibronectin, fibrin, basement membrane components or attachment peptides. Biologically active compounds such as anti-inflammatory agents may also be contained in the matrix. In the method, the matrix containing endothelial cells is implanted in a patient at a site adjacent the injury such as by wrapping the matrix around the blood vessel. The endothelial cells secrete products that diffuse into surrounding tissue but do not migrate to the endothelial cell lining of the blood vessel. The endothelial cells may be obtained by biopsy of the patient into which the matrix is implanted and the cells can be cultured in the matrix in vitro and then implanted in vivo.

OTHER PUBLICATIONS

McNamara, et al., "L–Arginine Inhibits Balloon Catheter–Induced Intimal Hyperplasia," *Biochem. Biophys. Res. Comm.* 193(1):291–296 (1993).

Moncada, et al., "The L–Arginine–Nitric Oxide Pathway," *N. Engl. J. Med.* 329(27):2002–2012 (1993).

Montesano, et al., "Basic Fibroblast Growth Factor Induces Angiogenisis in Vitro," *Proc. Natl. Acad. Sci. USA* 83:7297–7301 (1986).

Montañez, et al. "Comparative Study of Tube Assembly in Three–Dimensional Collagen Matrix and on Matrigel Coats," *Angiogenesis* 5:167–172 (2002).

Nugent, et al., "Vascular Cell–Derived Heparan Sulfate Shows Coupled Inhibition of Basic Fibroblast Growth Factor Binding and Mitogenesis in Vascular Smooth Muscle Cells," *Circulation Research* 73(6):1051–1060 (1993).

Rahmanian, et al., "Testicular Hyaluronidase Induces Tubular Structures of Endothelial Cells Grown in Three–Dimensional Colagen Gel through a CD44–Mediated Mechanism" *Int. J. Cancer* 97:601–607 (2002).

Reidy, et al., "Factors Controlling Smooth–Muscle Cell Proliferation," *Arch. Pathol Lab Med.* 116:1276–80 (1992).

Reidy, et al., "Neointimal Proliferation: the Role of Basic FGF on Vascular Smooth Muscle Cell Proliferation," *Thromb. Haemost.* 70(1):172–176 (1993).

Satake, et al., "Angiogenic Stimuli Are Essential for Survival of Vascular Endothelial Cells in Three–Dimensional Collagen Lattice" *Biochem. Biophys. Res. Comm.* 244:642–646 (1998).

Schwartz, et al., "The Aortic Intima; II. Repair of the Aortic Lining after Mechanical Denudation," *Am. J. Pathol.* 81:15–42 (1975).

Castellot, J. et al., "Cultured Endothelial Cells Produce a Heparinlike Inhibitor of Smooth Muscel Cell Growth," *Journal of Cell Biology*, 90:372–379 (1981) (already considered).

Centra, M. et al., "Culture of Bo vine Pulmonary Artery Endothelial Cells on Gelfoam Blocks," *FASEB J.*, 6:3117–3121 (1992).

Clowes, A. et al., "Kinetics of Cellular Proliferation After Arterial Injury I: Smooth Muscel Growth in the Absence of Endothelium," *Lab. Invest.*, 49:327–333 (1983).

Conte, M. et al., "Efficient Repopulation of Denuded Rabbit Arteries With Autologous Genetically Modified Endothelial Cells," *Circulation, 89:2161–69* (1994).

Conte, M. et al., "Endothelial Cell Seeding Fails to Attenuate Intimal Thickening in Balloon Injured Rabbit Arteries," *Journal of Vascular Surgery*, 21(3):413–421 (Mar., 1995).

Edelman, et al., "Effect of Controlled Adventitial Heparin Delivery on Smooth Muscle Cell Proliferation Following endothelial Injury," *Proc. Natl. Acad. Sci. (USA)*, 87:3773–3777 (1990).

Edelman, et al., "Perivascular and Intravenous Administration of Basic Fibroblast Growth Factor: Vascular and Solid Organ Deposition," *Proc. Natl. Acad. Sci. (USA)*, 90:1513–1517 (1993).

Edelman, et al., "Protamine and Protamine–Insulins Exacerbate the Vascular Response to Injury," *J. Clin. Invest.* 91:2308–2313 (1993).

Esko, J., "Animal Cell Mutants Defective in Heparan Sulfate Polymerization," *Heparin and Related Polysaccharides*, (Lane, Bjork, & Lindahl, Eds.) Plenum Press, pp 97–106 (1992).

Lee, Y. et al., "Endothelial Cell Seeding Onto the Extracellular Matrix of Fibroblasts for the Development of a Small Diameter Polyurethane Vessel," *ASAIO Journal*, 39(3):M740–M745.

Lehmann et al., "Paradoxical increase in Restenosis Rate With Chronic Heparin Use: Final Results of a Randomized Trial," *Journal Am. Coll. Cardiol.*, 17(2):181A (Abstract)(1991).

Nathan, et al., "Perivascular Heparin Delivery Using Biodegradable Polymers," *Polymeric Materials Science and Engineering.*, 70:320–321 (Proceedings of the American Chemical Society, Spring Meeting 1994).

Nathan, A. et al., "Tissue Engineered Perivascular Endothelial Cell Implants Regulate Vascular Injury," *Proc. Natl. Acad. Sci. (USA)*, 92:8130–8134 (1995).

Rapraeger, A. et al., "A Quantative Solid–Phase Assay for Identifying Radiolabeled Glycosaminoglycans in Crude Cell Extracts," *Analytical Biochemistry*, 179(2):361–365 (1989).

Westerband, et al., "Immunocytochemcial Determination of Cell Type and Proliferation Rate in Human Vein Graft Stenoses," *J. Vascular Surgery*, 25(1997).

\* cited by examiner

US 5,766,584 C1

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 11–19 are determined to be patentable as amended.

Claims 2–10, dependent on an amended claim, are determined to be patentable.

New claims 20–37 and 38 are added and determined to be patentable.

1. A method of inhibiting mechanisms involved in restenosis of a blood vessel having an endothelial cell lining following injury to the endothelial cell lining of the blood vessel of a patient in need of treatment thereof comprising:
implanting a biocompatible matrix [having seeded therein or thereon dissociated] *comprising engrafted* vascular endothelial cells at a site adjacent to the injury to the endothelial cell lining, wherein the vascular endothelial cells are provided in an amount effective to inhibit smooth muscle cell proliferation at the site of the injury [without migration of] *and wherein* the vascular endothelial cells *do not migrate* to the endothelial cell lining of the blood vessel *or give rise to cells which migrate to the endothelial cell lining of the blood vessel*.

11. [A composition] *An implantable device* for inhibiting mechanisms involved in restenosis of a blood vessel having an endothelial cell lining following injury to the endothelial cell lining of the blood vessel in a patient in need of treatment thereof, *the implantable device* comprising a biocompatible matrix shaped for implantation adjacent to [a] *an exterior surface of a blood vessel and in an amount sufficient to wrap an exterior surface of a* blood vessel *following injury*, the matrix [having seeded therein or thereon dissociated] *comprising engrafted* vascular endothelial cells, wherein the vascular endothelial cells are in an amount effective to inhibit smooth muscle cell proliferation at the site of the injury [without migration of] *and wherein the* vascular endothelial cells *do not migrate* to the endothelial cell lining of the blood vessel *or give rise to cells which migrate to the endothelial cell lining of the blood vessel*.

12. The [composition] *implantable device* of claim 11 wherein the *effective* amount is *an amount* effective to treat an injury arising from angioplasty, coronary artery bypass surgery, peripheral bypass surgery, or organ transplantation.

13. The [composition] *implantable device* of claim 11 wherein the matrix is in a form selected from the group consisting of gels, foams, suspensions, microcapsules, solid polymeric supports, and fibrous structures.

14. The [composition] *implantable device* of claim 11 wherein the cells are selected from the group consisting of autologous cells, allograft cells, and xenograft cells.

15. The [composition] *implantable device* according to claim [4] *11* wherein the matrix is biodegradable.

16. The [composition] *implantable device* of claim 15 wherein the matrix is formed of a material selected from the group consisting of polyhydroxy acids, polyorthoesters, polyanhydrides, proteins, polysaccharides, polyphosphazenes, and combinations thereof.

17. The [composition] *implantable device* of claim 11 wherein the matrix is formed of a material selected from the group consisting of ethylene vinyl acetate, polyvinyl alcohol, silicone, polyurethane, non-biodegradable polyesters, polyethyleneoxide-polypropyleneoxide, tetrafluoroethylene, and combinations thereof.

18. The [composition] *implantable device* of claim 11 wherein the matrix further comprises biologically active compounds selected from the group consisting of prostaglandins, prostanoids, tyrosine kinase inhibitors, immunosuppressants, glucocorticoids, anti-oxidants, free radical scavengers, peptide hormones, angiogenic factors, angiogenic inhibitory factors, and combinations thereof.

19. The [composition] *implantable device* of claim 14 wherein the cells are genetically engineered.

20. *An implantable device for inhibiting mechanisms involved in restenosis of a blood vessel having an endothelial cell lining following injury to the endothelial cell lining of the blood vessel in a patient in need of treatment thereof, the implantable device comprising a biocompatible matrix strip shaped for implantation adjacent to and in an amount sufficient to wrap around the exterior surface of the blood vessel, the matrix comprising engrafted vascular endothelial cells, wherein the vascular endothelial cells are in an amount effective to inhibit smooth muscle cell proliferation at the site of the injury and wherein the vascular endothelial cells do not migrate to the endothelial cell lining of the blood vessel or give rise to cells which migrate to the endothelial cell lining of the blood vessel.*

21. *An implantable device for inhibiting mechanisms involved in restenosis of a blood vessel having an endothelial cell lining following injury to the endothelial cell lining of the blood vessel in a patient in need of treatment thereof, the implantable device comprising a biocompatible matrix shaped for implantation adjacent to and in an amount sufficient to wrap an exterior surface of a blood vessel following injury, the matrix comprising engrafted vascular endothelial cells wherein the vascular endothelial cells are in an amount effective to inhibit smooth muscle cell proliferation at the site of the injury and wherein the vascular endothelial cells do not migrate to the endothelial cell lining of the blood vessel or give rise to cells which migrate to the endothelial cell lining of the blood vessel, the matrix in a form selected from the group consisting of gels, foams, and suspensions.*

22. *The method of claim 1 wherein the vascular endothelial cells are aortic endothelial cells.*

23. *The method of claim 22 wherein the aortic endothelial cells are bovine aortic endothelial cells.*

24. *The implantable device of any one of claims 11, 20 and 21 wherein the vascular endothelial cells are aortic endothelial cells.*

25. *The implantable device of claim 24 wherein the aortic endothelial cells are bovine aortic endothelial cells.*

26. *The method of claim 1 wherein the vascular endothelial cells are genetically engineered.*

27. *The implantable device of any one of claims 20 or 21 wherein the vascular endothelial cells are genetically engineered.*

28. *The method of claim 1 wherein the vascular endothelial cells secrete heparan sulfate.*

29. *The method of claim 28 wherein the vascular endothelial cells secrete heparan sulfate in an amount of at least about 1.2 micrograms per $10^6$ cells per day.*

30. The implantable device of any one of claims 11, 20, and 21 wherein the vascular endothelial cells secrete heparan sulfate.

31. The implantable device of claim 30 wherein the vascular endothelial cells secrete heparan sulfate in an amount of at least about 1.2 micrograms per $10^6$ cells per day.

32. The implantable device of any one of claims 20 or 21 wherein the effective amount is an amount effective to treat an injury arising from angioplasty, coronary artery bypass surgery, peripheral bypass surgery, or organ tranplantation.

33. The implantable device of any one of claims 20 or 21 wherein the cells are selected from the group consisting of autologous cells, allograft cells, and xenograft cells.

34. The implantable device of any one of claims 20 or 21 wherein the matrix is biodegradable.

35. The implantable device of claim 44 wherein the matrix is formed of a material selected from the group consisting of polyhydroxy acids, polyorthoesters, polyanhydrides, proteins, polysaccharides, polyphosphazenes, and combinations thereof.

36. The implantable device of any one of claims 20 or 21 wherein the matrix is formed of a material selected from the group consisting of ethylene vinyl acetate, polyvinyl alcohol, silicone, polyurethane, non-biodegradable polyesters, polyethyleneoxide-polypropyleneoxide, tetrafluoroethylene, and combinations thereof.

37. The implantable device of any one of claims 20 or 21 wherein the matrix further comprises biologically active compounds selected from the group consisting of prostaglandins, prostanoids, tyrosine kinase inhibitors, immunosuppressants, glucocorticoids, anti-oxidants, free radical scavengers, peptide hormones, angiogenic factors, angiogenic inhibitory factors, and combinations thereof.

38. The implantable device of any one of claims 11, 20, or 21, wherein the matrix comprises gelatin.

* * * * *